(12) United States Patent
Vardi

(10) Patent No.: US 10,765,797 B2
(45) Date of Patent: Sep. 8, 2020

(54) DEVICE FOR CONTROLLING FLUID DELIVERY

(71) Applicant: Gil Vardi, St. Louis, MO (US)

(72) Inventor: Gil Vardi, St. Louis, MO (US)

( * ) Notice: Subject to any disclaimer, the term of this patent is extended or adjusted under 35 U.S.C. 154(b) by 154 days.

(21) Appl. No.: 15/962,959

(22) Filed: Apr. 25, 2018

(65) Prior Publication Data

US 2018/0311432 A1 Nov. 1, 2018

Related U.S. Application Data

(60) Provisional application No. 62/490,147, filed on Apr. 26, 2017.

(51) Int. Cl.

| | |
|---|---|
| *A61M 5/00* | (2006.01) |
| *A61M 5/315* | (2006.01) |
| *A61M 5/31* | (2006.01) |
| *A61M 39/24* | (2006.01) |

(52) U.S. Cl.
CPC .......... *A61M 5/007* (2013.01); *A61M 5/3137* (2013.01); *A61M 5/31513* (2013.01); *A61M 39/24* (2013.01); *A61M 2005/3115* (2013.01); *A61M 2039/2473* (2013.01)

(58) Field of Classification Search
CPC .. A61M 5/007; A61M 39/24; A61M 5/31513; A61M 2039/2473; A61M 2005/3115
See application file for complete search history.

(56) References Cited

U.S. PATENT DOCUMENTS

| | | | |
|---|---|---|---|
| 5,575,767 A | 11/1996 | Stevens | |
| 6,019,747 A | 2/2000 | McPhee | |
| 6,050,957 A * | 4/2000 | Desch | A61B 5/15003 600/579 |
| 6,716,187 B1 * | 4/2004 | Jorgenson | A61M 1/029 206/223 |
| 7,927,305 B2 | 4/2011 | Yribarren et al. | |
| 9,050,400 B2 | 6/2015 | Shapland et al. | |
| 9,320,846 B2 | 4/2016 | Burns et al. | |
| 2002/0128611 A1 | 9/2002 | Kandalaft | |
| 2012/0024987 A1 | 2/2012 | Nacken | |

* cited by examiner

*Primary Examiner* — Bradley J Osinski
(74) *Attorney, Agent, or Firm* — David H. Chervitz

(57) ABSTRACT

A device for controlling delivery of a fluid to a patient is disclosed having an injector device having a cylindrical body and a plunger having a head having a valve, the valve capable of opening and closing, the plunger for insertion into the cylindrical body of the injector device. A device for controlling delivery of a fluid to a patient is also disclosed having an inlet end, an outlet end, a side having a portion of elastic material, the elastic material capable of expanding or contracting with the device for insertion between an injector device and a manifold or an injector device and a catheter.

5 Claims, 9 Drawing Sheets

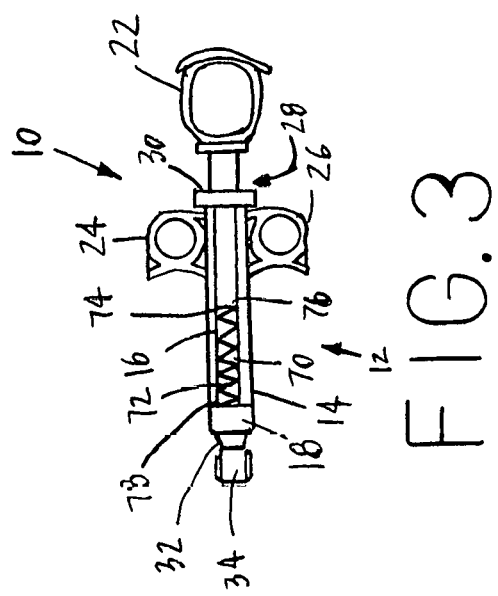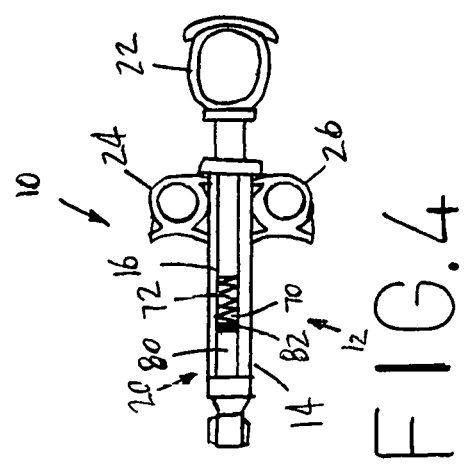

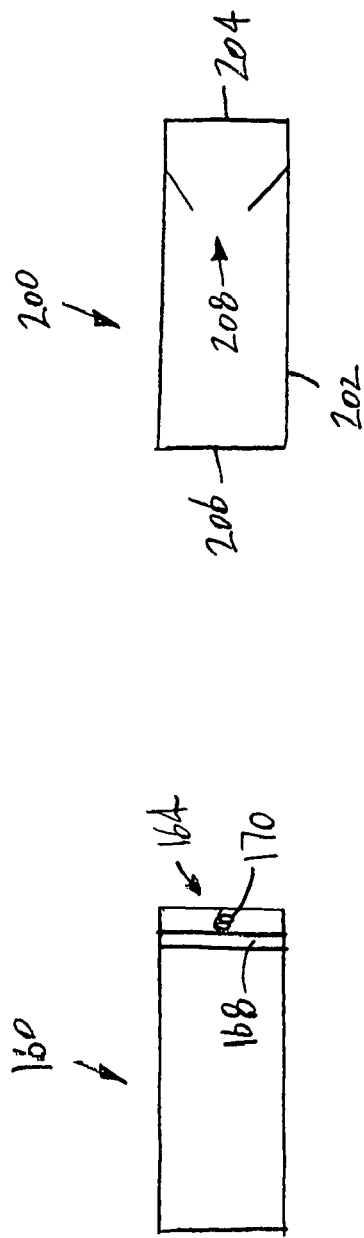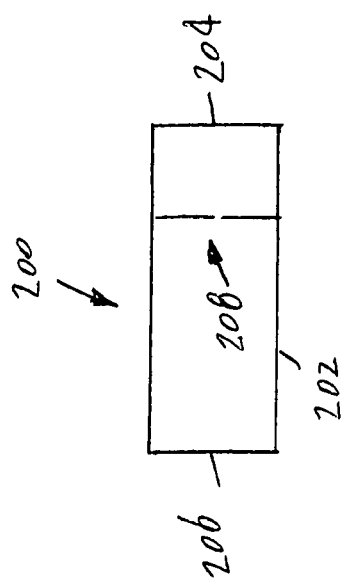

DEVICE FOR CONTROLLING FLUID DELIVERY

RELATED APPLICATION

This application claims priority to of U.S. Provisional Patent Application No. 62/490,147, filed on Apr. 26, 2017, the disclosure of which is incorporated herein by reference.

BACKGROUND

This disclosure relates to a medical device and more particularly to a device used to control or modulate delivery of a fluid to a patient during a medical procedure.

There are some medical procedures that require that a fluid be delivered to a specific body part or site within a human body. One such procedure is the delivery of a contrast agent within a human body for the diagnosis or treatment of coronary vascular disease. For example, a contrast agent may be used during an angiography or angioplasty and the placement of a stent. The contrast agent is introduced into the blood stream and an X-ray or fluoroscopic image is taken to assist a physician in diagnosis or treatment of the heart. Although the use of the contrast agent is employed, there is a concern that injection of too much of the contrast agent within the body could be harmful or toxic. In particular, Contrast Induced Nephropathy (CIN) is a form of kidney damage caused by the effects of dyes or radiopaque contrast media or agents used by cardiologists to image the heart during a heart procedure. The dye used may be toxic and too much of the dye may cause damage to the kidneys or failure of the kidneys. It is also possible that a patient may not be healthy enough to have a contrast agent used. However, the physician may want to take the risk and use the contrast agent in order to diagnose or treat the patient. In this case, it may be required to reduce the amount of contrast agent used in an attempt to reduce the damage that the agent may cause.

In an attempt to reduce the amount of contrast agent introduced into the patient various other less toxic chemicals have been used. However, such chemicals may reduce the visibility of the image produced. Another attempt has been to employ a collection system in which the contrast agent is collected downstream after an image has been produced. Yet, this requires a complex system and an individual to operate the collection system. Another attempt has been the use of an automated system to inject the contrast agent. The automated system tends to be expensive, cumbersome to use in a lab, and require training to properly use to gain experience in the use of the automated system.

Therefore, it would be desirable to have a device for controlling fluid delivery during a medical procedure to limit the amount of fluid being injected or introduced into a human body. It would be advantageous to have a device for controlling fluid delivery that is capable of being used with a manifold delivery system and a catheter system. It would also be advantageous to have a device for controlling fluid delivery that may be easily manipulated or used by a physician to control the amount of a contrast agent being introduced into a human body during diagnosis or treatment of an organ.

SUMMARY

In one form of the present disclosure, a device for controlling delivery of a fluid to a patient is disclosed which comprises an injector device having a cylindrical body and a plunger having a head having a valve, the valve capable of opening and closing, the plunger for insertion into the cylindrical body of the injector device.

In another form of the present disclosure, a device for controlling delivery of a fluid to a patient comprises an injector device having a cylindrical body, a plunger having a head having, the plunger for insertion into the cylindrical body of the injector device, and an exterior collecting tube having a pair of valves that are capable of opening and closing to allow fluid to enter into the collecting tube or exit from the collecting tube.

In yet another form of the present disclosure, a device for controlling delivery of a fluid comprises a cylindrical body having a first end and a second end, a valve cap positioned within the cylindrical body, a post positioned at the first end of the cylindrical body, and a spring having a first end connected to the valve cap and a second end connected to the post.

In still another embodiment of the present disclosure, a device for controlling delivery of a fluid comprises a cylindrical body having a first end and a second end and a valve positioned within the cylindrical body.

In another embodiment of the present disclosure, a device for controlling delivery of a fluid to a patient is provided which discloses an injector device having a cylindrical body and a plunger having a head having a central portion having an elastic material, the elastic material capable of expanding and contracting, the plunger for insertion into the cylindrical body of the injector device.

In still another embodiment, a device for controlling delivery of a fluid to a patient comprises an injector device having a cylindrical body and a plunger having a head having a number of pores, the pores capable of opening and closing, the plunger for insertion into the cylindrical body of the injector device.

In another form of the present disclosure, a device for controlling delivery of a fluid to a patient comprises an injector device having a cylindrical body and a plunger having an inlet end, an outlet end, a side having a portion of elastic material, the elastic material capable of expanding or contracting, the plunger for insertion into the cylindrical body of the injector device.

In yet another embodiment of the present disclosure, a device for controlling delivery of a fluid to a patient comprising an inlet end, an outlet end, a side having a portion of elastic material, the elastic material capable of expanding or contracting with the device for insertion between an injector device and a manifold or an injector device and a catheter.

In still another embodiment of the present disclosure, a device for controlling delivery of a fluid to a patient is disclosed which comprises an injector device having a cylindrical body, and a plunger having a head having an opening having a valve connected to a movable tooth member, and a partial hollow interior, the plunger for insertion into the cylindrical body of the injector device.

In light of the foregoing comments, it will be recognized that the present disclosure provides a device for controlling fluid delivery during a medical procedure.

The present disclosure provides a device for controlling fluid delivery that may be used to reduce the amount of a contrast agent introduced into a body of a patient during a medical procedure.

The present disclosure provides a device for controlling fluid delivery that is easy to use and can be employed with highly reliable results.

The present disclosure provides a device for controlling fluid delivery that may be constructed using readily available parts and components.

The present disclosure is also directed to a device for controlling fluid delivery that may be used to provide a contrast agent to a heart during diagnosis or treatment of the heart.

These and other advantages of the present device for controlling fluid delivery will become apparent after considering the following detailed specification in conjunction with the accompanying drawings, wherein:

BRIEF DESCRIPTION OF THE DRAWINGS

FIG. 3 is a cross-sectional view of the device for controlling fluid delivery shown in FIG. 1 shown in a closed position;

FIG. 4 is a cross-sectional view of the device for controlling fluid delivery shown in FIG. 1 shown in an open position;

FIG. 11 is a perspective view of another embodiment of a device for controlling fluid delivery constructed according to the present disclosure connected to a manifold delivery system;

FIG. 12 is a perspective view of another embodiment of a device for controlling fluid delivery constructed according to the present disclosure connected to a manifold delivery system;

FIG. 13 is a perspective view of another embodiment of a device for controlling fluid delivery constructed according to the present disclosure connected to a manifold delivery system;

DETAILED DESCRIPTION OF A PREFERRED EMBODIMENT

Figure 1:
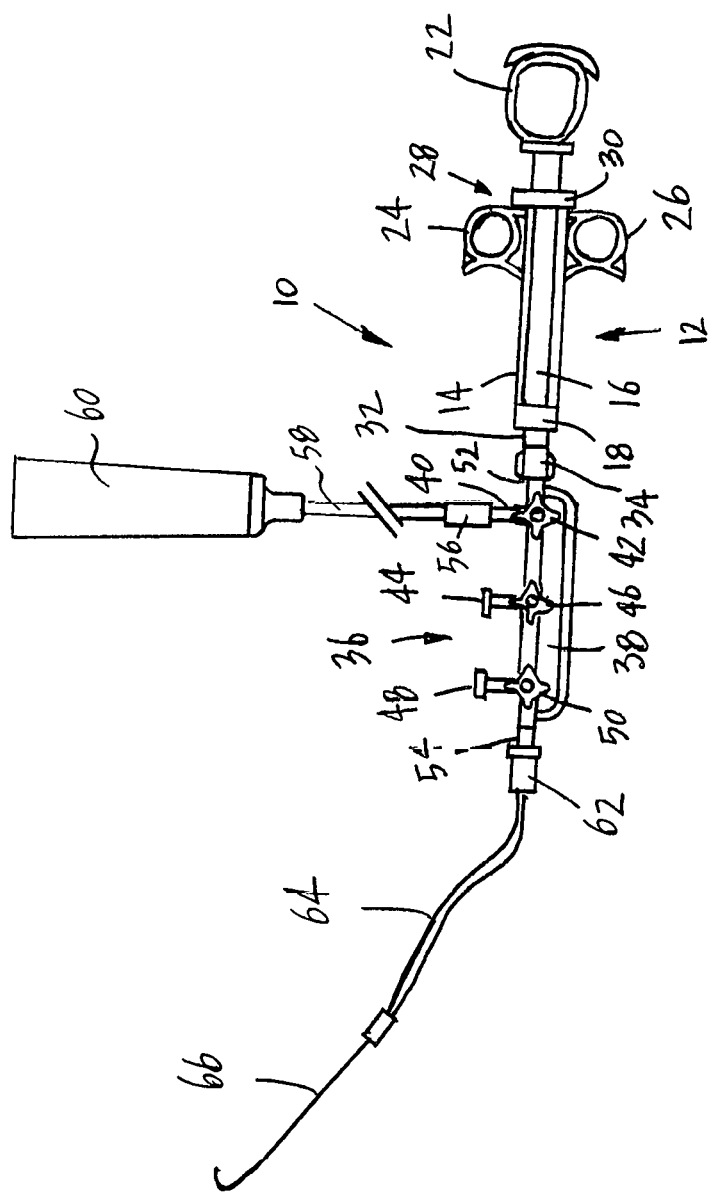
FIG. 1 is a perspective view of a device for controlling fluid delivery constructed according to the present disclosure connected to a manifold delivery system.
Figure 2:
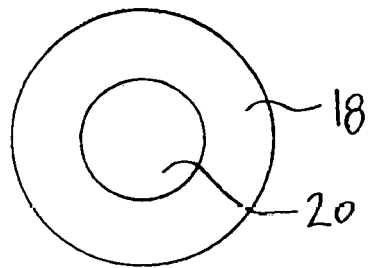
FIG. 2 is a front view of a plunger head associated with the device for controlling fluid delivery shown in FIG. 1.

Referring now to the drawings, wherein like numbers refer to like items, number 10 identifies a device for controlling medium delivery constructed according to the present disclosure. With reference now to FIGS. 1 and 2, the device 10 is shown to comprise an injector device 12 having a cylindrical body 14 and a plunger 16 having a head 18 having a valve 20 with the valve 20 capable of opening and closing. The plunger 16 is inserted into the cylindrical body 14 of the injector device 12 and may be moved within the cylindrical body 14 to suction in a fluid (not shown) or to push out the fluid. The injector device 12 may have a first finger grip 22 connected to the plunger 16 to facilitate movement of the plunger 16 within the cylindrical body 14. The injector device 12 may also have a pair of side finger grips 24 and 26 to hold or grasp the injector device 12. The injector device 12 has a first or back end 28 through which the plunger 16 may be inserted. The first end 28 may also have a locking cap 30 to secure the plunger 16 within the injector device 12. The injector device 12 also has a second or front end 32 through which fluid may flow into or out of the device 12. The second end 32 may have a connector device 34. The first end 28 has a diameter and the second end 32 has a diameter with the diameter of the first end 28 typically being greater than the diameter of the second end 32. The connector device 34 is connected to a manifold device 36.

The manifold device 36 has a body 38 having a first port 40 having a first stopcock 42, a second port 44 having a second stopcock 46, a third port 48 having a third stopcock 50, a first or inlet end 52, and a second or outlet end 54. The connector device 34 is connected to the inlet end 52 of the manifold device 36. The first port 40 is connected to a connector 56, a tubing 58, and a container 60. The container 60 may contain a fluid such as a contrast media for use in a medical procedure, as will be explained more fully herein. The outlet end 54 is connected to a connector 62, a tubing 64 within which is a catheter 66.

As can be appreciated, the device 10 is used in the following manner. The first stopcock 42 is positioned to allow any fluid in the container 60 to be drawn into the injector device 12. By moving the plunger 16 backwards, fluid may be drawn or sucked into the cylindrical body 14. Once a quantity of fluid has been drawn into the cylindrical body 14, the first stopcock 42 may be repositioned so that fluid within the cylindrical body 14 may be pushed out or sent into the body 38 of the manifold device 36. The second stopcock 46 and the third stopcock 50 are also positioned so that any fluid that enters into the body 38 may flow through the body 38 to the outlet end 54. Fluid will also be allowed to flow through the tubing 64 into a body part (not shown). As will be explained in more detail herein, the valve 20 in the head 18 is used to control the quantity of fluid that will be sent to the body 38 of the manifold device 36 and that will be injected into a body part. In this manner, fluid may be introduced into a body part in a controlled manner.

With reference now to FIG. 3, the plunger 16 of the device 10 is shown having a partial hollow interior 70 having a spring 72 having a first spring end 74 connected to or positioned against a back end 76 and a second spring end 78 positioned against the head 18 of the plunger 16. The spring 72 is capable of moving within the partial hollow interior 70. In this position, the spring 72 is in the closed position and the valve 20 (FIG. 2) is against the head 18 in the closed position. The device 10 is also shown to have the cylindrical body 14 and the first finger grip 22 connected to the plunger 16 to facilitate movement of the plunger 16 within the cylindrical body 14. The injector device 12 has the pair of side finger grips 24 and 26 to hold or grasp the injector device 12. The injector device 12 has the first end 28 through which the plunger 16 may be inserted. The first end 28 also has the locking cap 30 to secure the plunger 16 within the injector device 12. The injector device 12 also has the second or front end 32 having the connector device 34.

FIG. 4 illustrates the device 10 with the valve 20 in the open position. In this particular arrangement the spring 72 has been compressed and there is an area 80 within the partial hollow interior 70 in which fluid drawn into the plunger 16 may flow and be captured. When the valve 20 is in the open position, less of the fluid will be provided into the manifold device 36 (FIG. 1) than if the valve 20 is closed. The valve 20 also has a valve cap 82 attached to the spring 72. Further, depending on the spring constant of the spring 72 being used, a different area 80 may be presented for capturing different amounts of fluid in the area 80. For example, there may be some applications where only a small amount of fluid needs to be captured in the area 80. In this particular scenario, the spring 72 may have a stiffer spring constant. Also, if the area 80 needs to be large then the spring 72 will use a spring having a weaker spring constant. In this manner, the device 10 is capable of controlling fluid delivery from the device 10 to the tubing 64 (FIG. 1). The device 10 is also depicted having the injector device 12, the cylindrical body 14, the plunger 16, the first finger grip 22, and the pair of side finger grips 24 and 26.

Figure 5:
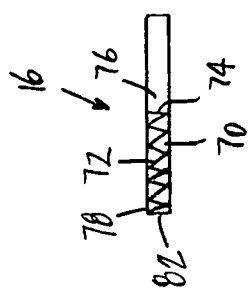
FIG. 5 is a partial perspective view of a plunger removed from the device for controlling fluid delivery with the plunger shown in the closed position.

As shown in FIG. 5, the plunger 16 has been removed from the device 10 to show more clearly the functioning of the plunger 16. As discussed, the plunger 16 has the partial hollow interior 70 having the spring 72 having the first spring end 74 connected to or positioned against the back end 76 and the second spring end 78 positioned against the head 18 of the plunger 16. The spring 72 is capable of moving within the partial hollow interior 70. In the particular orientation shown, the spring 72 is in the closed position and the valve cap 82 is against the head 18 (FIG. 2) in the closed position. In this position, no fluid is allowed to enter into the interior 70.

Figure 6:
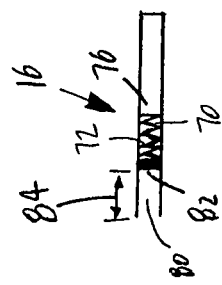
FIG. 6 is a partial perspective view of a plunger removed from the device for controlling fluid delivery with the plunger shown in the closed position.

Referring to FIG. 6, the plunger 16 is again shown being removed from the device 10 to illustrate the area 80 in which fluid may enter and be captured. The spring 72 has been compressed to move the valve cap 82 into the area 80. The valve cap 82 may move a distance 84 into the partial hollow interior 70. This distance 84 may be calculated or predetermined and the spring constant associated with the spring 72 assists in determining the distance 84. Again, the distance 84 can be made larger or smaller depending on the spring constant of the spring 72 being employed in the device 10. The back end 76 is also shown in this figure.

Figure 7:
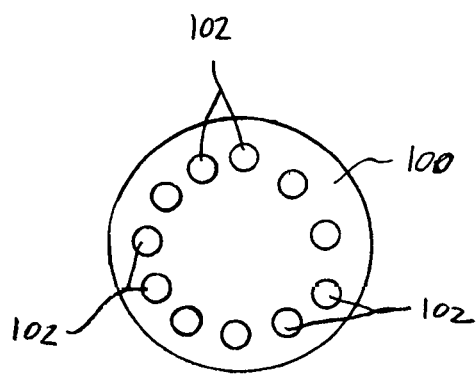
FIG. 7 is a front view of another embodiment of a plunger head associated with the device for controlling fluid delivery shown in FIG. 1.

FIG. 7 depicts another embodiment of a plunger head 100 constructed according to the present disclosure that may be used with the device 10 instead of the plunger head 18. The plunger head 100 has a number of openings 102 placed around the head 100. The openings 102 allow fluid to pass into the plunger 16 (FIG. 1). Fluid that is trapped or captured in the openings 102 assists in controlling the amount of fluid transferred to the manifold device 36 (FIG. 1). As can be appreciated, more or less of the openings 102 may be employed with the plunger head 100. For example, if the flow rate of fluid into the plunger 16 is to be increased then more of the openings 102 may be used. Also, if the flow rate of fluid into the plunger 16 is to be decreased then fewer of the openings 102 may be employed. It is also contemplated that the diameters of the openings 102 may be increased or decreased or that the openings may take on different shapes such as slits or slots.

Figure 8:
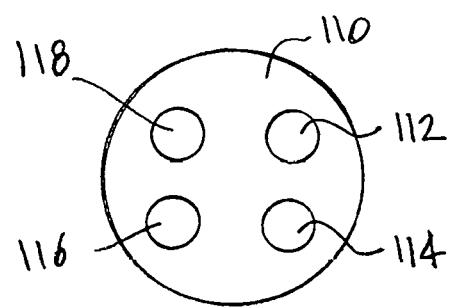
FIG. 8 is a front view of another embodiment of a plunger head associated with the device for controlling fluid delivery shown in FIG. 1.

With particular reference now to FIG. 8, another embodiment of a plunger head 110 constructed according to the present disclosure that may be used with the device 10 instead of the plunger head 18. The plunger head 110 is shown to comprise four valves 112, 114, 116, and 118 placed around the head 110. The valves 112, 114, 116, and 118 allow fluid to pass into the plunger 16 (FIG. 1). The valves 112, 114, 116, and 118 are similar in construction and operation as the valve 20. Also, it is possible that each valve 112, 114, 116, and 118 can have a spring that has a spring constant that is the same or different. In this manner, various amounts of fluid is capable of entering into the valves 112, 114, 116, and 118. openings 102 may be employed. It is also contemplated that the diameters of the openings 102 may be increased or decreased or that the openings may take on different shapes such as slits or slots.

Figure 9:
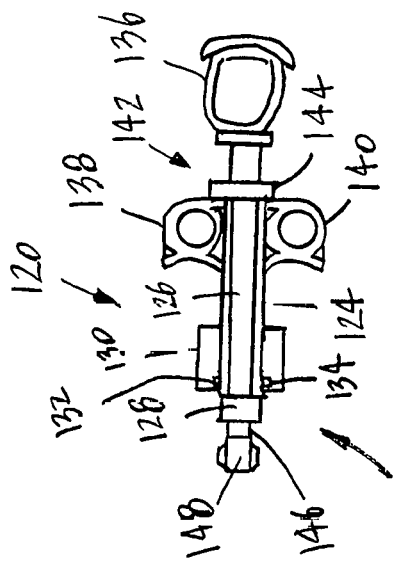
FIG. 9 is a perspective view of another embodiment of a device for controlling fluid delivery constructed according to the present disclosure connected to a manifold delivery system.

FIG. 9 illustrates another embodiment of a device for controlling fluid delivery 120 that may be used with the manifold device 36 (FIG. 1). The device 120 comprises an injector device 122 having a cylindrical body 124 and a plunger 126 having a head 128. The cylindrical body 124 has an exterior collecting tube or cylinder 130 and a pair of valves 132 and 134 that are capable of opening and closing to allow fluid to enter into the collecting tube 130 or exit from the collecting tube 130. As can be appreciated, any of the valves or elastic materials disclosed herein may be used for the valves 132 and 134. The plunger 126 is inserted into the cylindrical body 124 of the injector device 122 and may be moved within the cylindrical body 124 to suction in fluid or to push out fluid. The injector device 122 may have a first finger grip 136 connected to the plunger 126 to facilitate movement of the plunger 126 within the cylindrical body 124. The injector device 122 may also have a pair of side finger grips 138 and 140 to assist in holding or grasping the injector device 122. The injector device 122 has a first or back end 142 through which the plunger 126 may be inserted. The first end 142 may also have a locking cap 144 to secure the plunger 126 within the injector device 122. The injector device 122 also has a second or front end 146 having a connector device 148. The first end 142 has a diameter and the second end 146 has a diameter with the diameter of the first end 142 typically being greater than the diameter of the second end 146. The connector device 148 is adapted to be connected to the manifold device 36 shown in FIG. 1. The device 120 may be used to draw in fluid into both the cylindrical body 124 and the collecting tube 130 by use of the plunger 126 and the valves 132 and 134. Fluid may be trapped in the collecting tube 130 and fluid drawn into the cylindrical body 124 may be expelled or forced out the front end 146 by movement of the plunger 126 to force fluid into the manifold device 36 to be sent through the tubing 64 into a body part of a patient during a medical procedure.

Figure 10:
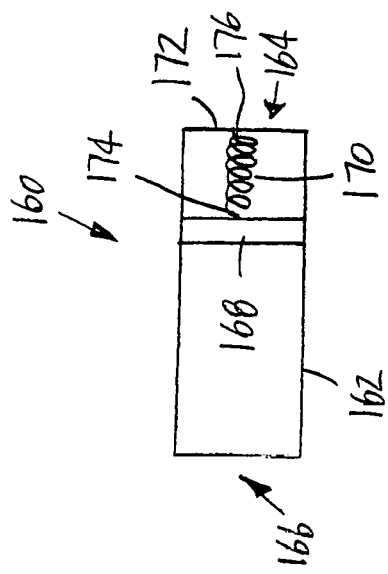
FIG. 10 is a perspective view of another embodiment of a device for controlling fluid delivery constructed according to the present disclosure connected to a manifold delivery system.

Referring now to FIG. 10, another embodiment of a device for controlling fluid delivery 160 is depicted. The device 160 may be connected between an injector device or syringe and the manifold device 36. The device 160 comprises a cylindrical body 162 having a first or back end 164, a second or front end 166, a valve cap 168, a spring 170, and spring holding post 172. The spring 170 has a first end 174 connected to the valve cap 168 and a second end 176 connected to the post 172. The device 160 is shown in an open position in which fluid may flow through the device 160. The first end 164 may be connected to a typical syringe and the second end 166 may be connected to a manifold device or a catheter. In operation, the syringe may be loaded with fluid and closing a plunger associated with the syringe will push fluid out of the syringe into the device 160 opening the valve cap 168 to allow fluid to flow out through the second end 166.

FIG. 11 illustrates is the device 160 in a closed position. In the closed position the device 160 prevents any fluid to flow through the device 160. The valve cap 168 is against the back end 164 covering the back end 164. The spring 170 has also been fully compressed.

With particular reference now to FIG. 12, another embodiment of a device for controlling fluid delivery 200 is shown. The device 200 may be connected between an injector device or syringe and the manifold device 36. The device 200 comprises a cylindrical body 202 having a first or back end 204, a second or front end 206, and a valve 208. The valve 208 is capable of opening only in one way. The device 200 is shown in an open position in which fluid may flow through the device 200. The first end 204 may be connected to a typical syringe and the second end 206 may be connected to a manifold device or a catheter. In operation, the syringe may be loaded with fluid and closing a plunger associated with the syringe will push fluid out of the syringe into the device 200 opening the valve 208 to allow fluid to flow out through the second end 206.

FIG. 13 illustrates is the device 200 in a closed position. In the closed position the device 200 prevents any fluid to flow through the device 200. The valve 208 is closed and no fluid may pass from the first end 204 through the body 202 and out the second end 206. In this manner, fluid may only flow one way through the device 200.

Figure 14:
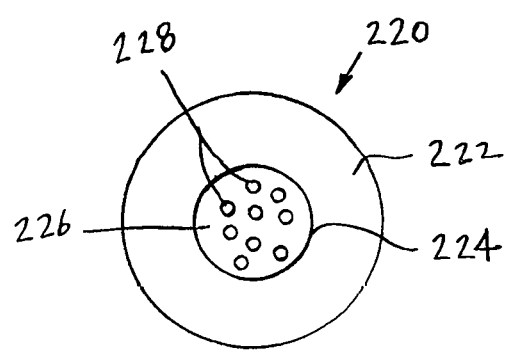
FIG. 14 is a front view of another embodiment of a plunger associated with the device for controlling fluid delivery shown in FIG. 1.

FIG. 14 a front view of another embodiment of a plunger 220 associated with the device for controlling fluid delivery 10 shown in FIG. 1. The plunger 220 has a plunger head 222 having a central portion 224 having an elastic material 226 that has a number of pores or valves 228 that allow fluid to flow there through. The pores 228 respond to pressure and will open to allow fluid to flow.

Figure 15:
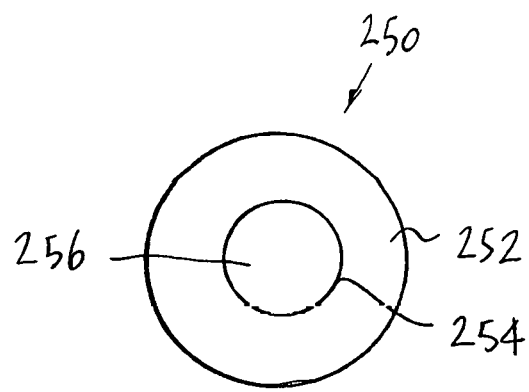
FIG. 15 is a front view of another embodiment of a plunger head associated with the device for controlling fluid delivery shown in FIG. 1.

Referring now to FIG. 15, a front view of another embodiment of a plunger 250 associated with the device for controlling fluid delivery 10 shown in FIG. 1 is depicted. The plunger 250 has a plunder head 252 having a central portion 254 constructed of an elastic or compliant material 256 that responds to pressure The elastic material is capable of expanding when pressure is detected or contracting when pressure is removed. Expansion of the elastic material 256 puts the plunger 250 in an active state and contraction of the elastic material 256 placed the plunger 250 in to an inactive or initial state.

Figure 16:
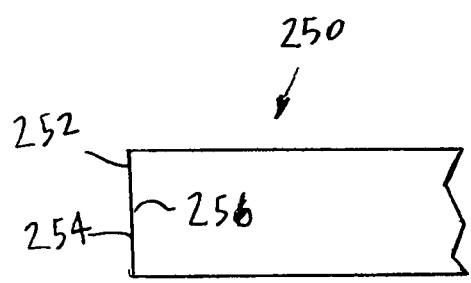
FIG. 16 is a partial side view of the plunger shown in FIG. 15 in an inactive state.

FIG. 16 is a partial side view of the plunger 250 shown in FIG. 15 illustrated in an inactive state. In the inactive state there is not enough pressure against the elastic material 256 to make the material 256 move to accept any fluid.

Figure 17:
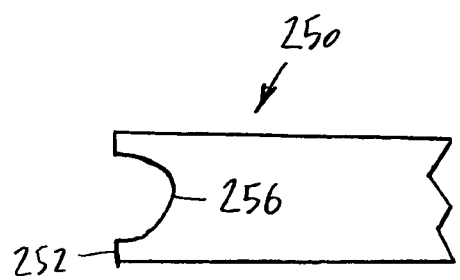
FIG. 17 is a partial side view of the plunger shown in FIG. 16 shown in an active state.

FIG. 17 is the plunger 250 shown in FIG. 16 depicted in an active state. In the active state there is enough pressure against the elastic material 256 to make the material 256 move or balloon to accept fluid therein. As can be appreciated, once the pressure against the elastic material 256 is removed, the elastic material 256 will return to the inactive state and fluid will be removed from the elastic material 256.

Figure 18:
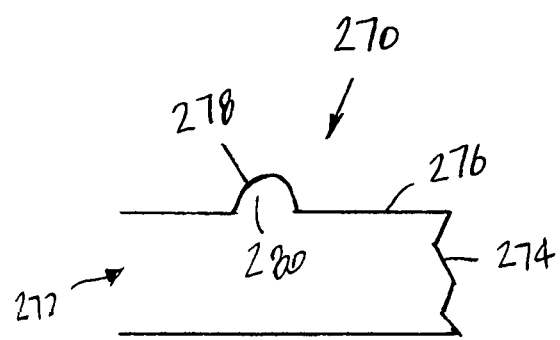
FIG. 18 is a partial side view of another embodiment of a plunger or a device associated with the device for controlling fluid delivery shown in FIG. 1 with the plunger shown in an active state.

With particular reference now to FIG. 18, a partial side view of another embodiment of a plunger 270 for use with the device for controlling fluid delivery 10 is illustrated. The plunger 270 comprises an inlet end 272, an outlet end 274, and a side 276 having a portion of elastic or compliant material 278. The elastic material 278 is shown in an active state in that fluid 280 has forced the elastic material 278 to expand to allow the fluid 280 to be captured therein. Once pressure is removed from the plunger 270, the fluid 280 will flow out of the inlet end 272 and the elastic material 278 will return to its original shape to an inactive state. The plunger 270 may also just be a device that may be inserted between an injector device, such as the injector device 12 (FIG. 1), and a manifold, such as the manifold device 34 (FIG. 1), or an injector device and a catheter, such as the catheter 66 (FIG. 1).

Figure 19:
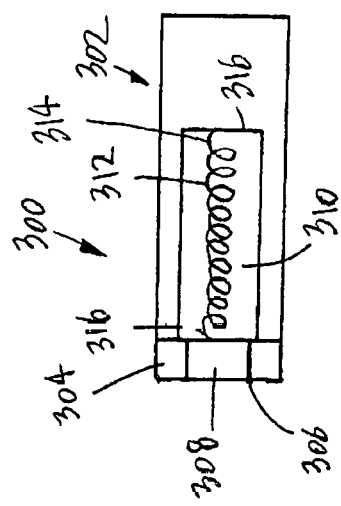
FIG. 19 is a cross-sectional view of another embodiment of a device for controlling fluid delivery constructed according to the present disclosure.

FIG. 19 shows a cross-sectional view of another embodiment of a device for controlling fluid delivery 300 constructed according to the present disclosure. The device 300 has a plunger 302 that has been removed from the device 10 to show more clearly the functioning of the plunger 302. The plunger 302 has a plunger head 304 that as an opening 306 having a disc, cap, or cylinder body 308 covering the opening 306. The plunger 302 has a partial hollow interior 310 having a spring 312 having a first spring end 314 connected to or positioned against a back end 316 of the partial hollow interior 310 and a second spring end 318 positioned against the disc body 308 of the head 304 of the plunger 302. The spring 312 is capable of moving within the partial hollow interior 310. In the particular orientation shown, the spring 312 is in the closed position and the disc body 308 in the closed position in the opening 306 in the head 304. In this position, no fluid is allowed to enter into the partial hollow interior 310. As can be appreciated, when the plunger 302 is pushed forward in order to inject fluid from the injector device 12 (FIG. 1) into a patient, as the pressure in the injector device 12 rises, the disc body 308 will move into the partial hollow interior 310 allowing fluid to enter into the partial hollow interior 310. In this manner, less fluid will be injected into a body. Although not shown, it is also contemplated that the plunger 302 may have markings thereon to provide a measurement for how much fluid is captured or saved within the partial hollow interior 310 and was not injected into the body. This measurement may also be accomplished by a ruler, by mechanical means, by light, and also transmitted by visual means or by radio or bluetooth.

Figure 20:
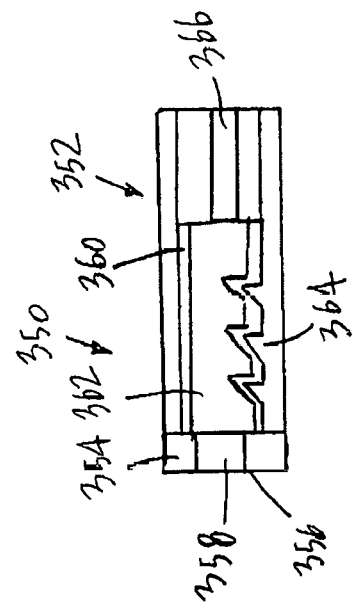
FIG. 20 is a cross-sectional view of another embodiment of a device for controlling fluid delivery constructed according to the present disclosure.

Referring now to FIG. 20, another embodiment of a device for controlling fluid delivery 350 is illustrated. The device 350 has a plunger 352 that has been removed from the device 10 to show more clearly the functioning of the plunger 352. The plunger 352 has a plunger head 354 that as an opening 356 having a disc, cap, or cylinder body 358 covering the opening 356. The plunger 352 has a partial hollow interior 360. The plunger head 354 is connected to a movable tooth or gear member 362 that mates with a stationary tooth or gear side 364. The movable tooth member 362 is also connected to a release mechanism 366. The movable tooth member 362 is capable of moving within the partial hollow interior 360. In this particular drawing, the movable tooth member 362 is in the closed position and the disc body 358 in the closed position in the opening 356 in the head 354. In this position, no fluid is allowed to enter into the partial hollow interior 360. As can be appreciated, when the plunger 352 is pushed forward in order to inject fluid from the injector device 12 (FIG. 1) into a patient, as the pressure in the injector device 12 rises, the disc body 358 and the movable tooth member 362 will move into the partial hollow interior 360 allowing fluid to enter into the partial hollow interior 360. Since, in essence, some fluid is trapped within the partial hollow interior 360 less fluid will be injected into a body or a body part. In order to move the disc body 358 back into the closed position in the opening 356, the release mechanism 366 is operated in which the movable tooth member 362 is released from the stationary tooth side 364 which allows the disc body 358 to slide or move back into the closed position. Markings may also be provided on the plunger 352, as discussed above, to indicate how much fluid has been saved.

From all that has been said, it will be clear that there has thus been shown and described herein a device for controlling delivery of fluid to a patient which fulfills the various advantages sought therefore. It will become apparent to those skilled in the art, however, that many changes, modifications, variations, and other uses and applications of the subject device for controlling delivery of fluid are possible and contemplated. All changes, modifications, variations, and other uses and applications which do not depart from the spirit and scope of the disclosure are deemed to be covered by the disclosure, which is limited only by the claims which follow.

What is claimed is:

1. A device for controlling delivery of a fluid to a patient comprising:

an injector device having a cylindrical body having a front end having an opening through which fluid may flow into or out of the cylindrical body and a back end having an opening, and a connector device at the front end; and a plunger having a head having an opening and the plunger further having a valve cap, the valve cap capable of opening and closing the opening in the head, the plunger for insertion into the cylindrical body of the injector device, the plunger further having a partial hollow interior having a back end, a spring having a first spring end and a second spring end, the first spring end connected to the back end of the partial hollow interior and the second end connected to the valve cap adjacent to the opening in the head, the partial hollow interior for capturing fluid when the spring moves the valve cap away from the opening in the head.

2. The device of claim 1 further comprising a manifold device having a body having a first port having a first stopcock, a second port having a second stopcock, a third port having a third stopcock, an inlet end, and an outlet end, the connector device connected to the inlet end of the manifold device.

3. The device of claim 2 wherein the first port is connected to a connector, a tubing, and a container containing a fluid that may flow into the injector device.

4. The device of claim 1 wherein the valve cap may move a distance into the partial hollow interior to allow fluid to flow and be captured within the space when the spring is compressed.

5. The device of claim 1 wherein any fluid captured within the partial hollow interior may flow out through the opening in the front end.

* * * * *